United States Patent [19]

Sakai et al.

[11] Patent Number: 4,979,513
[45] Date of Patent: Dec. 25, 1990

[54] ULTRASONIC DIAGNOSTIC APPARATUS

[75] Inventors: Ikuo Sakai; Nobuaki Furuya, both of Kawasaki; Yasuhiro Nakamura, Tokyo; Masami Kawabuchi, Yokohama, all of Japan

[73] Assignee: Matsushita Electric Industrial Co., Ltd., Japan

[21] Appl. No.: 254,834

[22] Filed: Oct. 7, 1988

[30] Foreign Application Priority Data

| Oct. 14, 1987 | [JP] | Japan | 62-258865 |
| Oct. 14, 1987 | [JP] | Japan | 62-258866 |
| Oct. 14, 1987 | [JP] | Japan | 62-258863 |
| Oct. 14, 1987 | [JP] | Japan | 62-258864 |
| Oct. 14, 1987 | [JP] | Japan | 62-258867 |
| Oct. 14, 1987 | [JP] | Japan | 62-258868 |
| Jun. 15, 1988 | [JP] | Japan | 63-147452 |

[51] Int. Cl.⁵ .................................... A61B 8/00
[52] U.S. Cl. ........................ 128/661.09; 73/861.25
[58] Field of Search .............. 128/661.08–661.1; 73/861.25

[56] References Cited

U.S. PATENT DOCUMENTS

| 4,265,126 | 5/1981 | Papadofiangolis et al. ... 128/661.09 X |
| 4,660,565 | 4/1987 | Shirasaka ........................ 128/261.09 |
| 4,693,319 | 9/1987 | Amemiya ........................ 73/861.25 X |
| 4,742,830 | 5/1988 | Tamano et al. ................ 128/661.09 |
| 4,744,367 | 5/1988 | Kodama et al. ................ 128/661.09 |
| 4,759,375 | 7/1988 | Namehawa ..................... 128/661.09 |
| 4,790,232 | 12/1988 | Leavitt et al. ................. 128/661.09 |
| 4,790,322 | 12/1988 | Iinuma ........................... 128/661.1 |
| 4,800,891 | 1/1989 | Kim ............................... 128/661.09 |

FOREIGN PATENT DOCUMENTS

| 0081045 | 6/1983 | European Pat. Off. . |
| 0144968 | 6/1985 | European Pat. Off. . |
| 3605164 | 8/1986 | Fed. Rep. of Germany . |
| 58-188433 | 11/1983 | Japan . |
| 8502105 | 5/1985 | PCT Int'l Appl. . |

Primary Examiner—Francis Jaworski
Attorney, Agent, or Firm—Lowe, Price, Leblanc, Becker & Shur

[57] ABSTRACT

Pulses of an ultrasonic wave beam are emitted into a body at a predetermined repetition period. Echo pulses of the ultrasonic wave beam are received via a plurality of different channels. Each of the received pulses is converted simultaneously into corresponding electric signals of the respective channels. A time-dependent change in a variation between the electric signals of the respective channels is derived. A component of a speed of moving matter within the body in a predetermined direction is calculated on the basis of the derived time-dependent change. The moving matter causes the echo pulses. The predetermined direction is perpendicular to a direction of travel of the ultrasonic wave beam pulses.

18 Claims, 15 Drawing Sheets

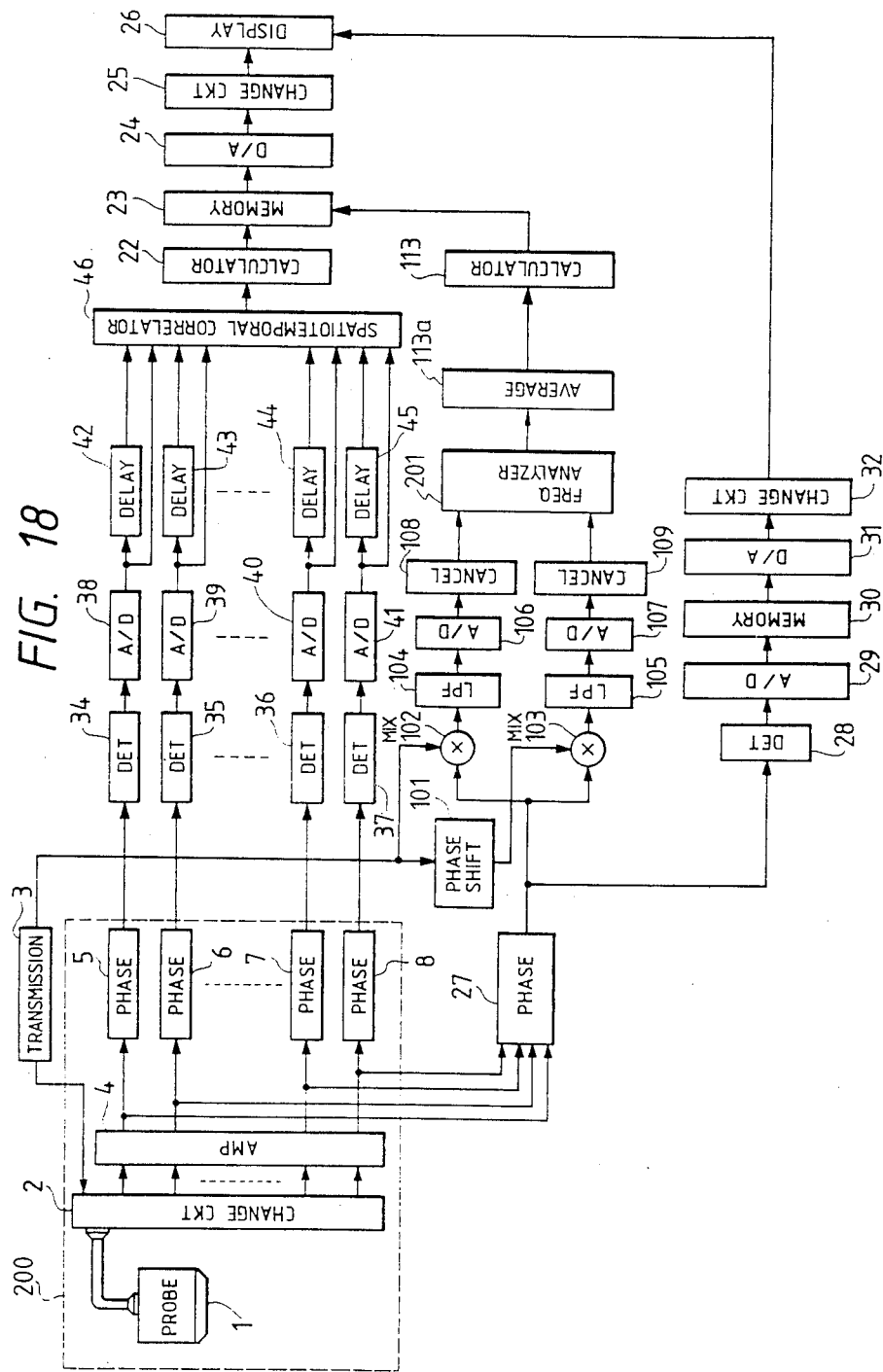

ULTRASONIC DIAGNOSTIC APPARATUS

BACKGROUND OF THE INVENTION

1. Field of the Invention

This invention relates to an ultrasonic diagnostic apparatus measuring and indicating a distribution of speeds of moving liquid, flowing blood, or other moving portions within a body.

2. Description of the Prior Art

Japanese published unexamined patent application 58-188433 discloses an ultrasonic diagnostic apparatus measuring and indicating a distribution of speeds of moving portions of a body. This prior-art apparatus uses the Doppler effect in determining the speeds. In the prior art apparatus, the use of the Doppler effect makes it impossible to detect components of speeds in directions perpendicular to directions of travel of ultrasonic waves. The undetected speed components tend to cause unreliable measurement and indication of a distribution of speeds.

SUMMARY OF THE INVENTION

It is an object of this invention to provide an ultrasonic diagnostic apparatus which measures and indicates a component of a speed of a moving body portion liquid in a direction perpendicular to a direction of travel of an ultrasonic wave beam.

It is another object of this invention to provide an ultrasonic diagnostic apparatus which accurately measures and indicates a distribution of speeds of moving portions or liquid of a body.

In a first ultrasonic diagnostic apparatus of this invention, pulses of an ultrasonic wave beam are emitted into a body at a predetermined repetition period. Echo pulses of the ultrasonic wave beam are received via a plurality of different channels. Each of the received pulses is converted simultaneously into corresponding electric signals of the respective channels. A time-dependent change in a variation between the electric signals of the respective channels is derived. A component of a speed of moving matter within the body in a predetermined direction is calculated on the basis of the derived time-dependent change. The moving matter causes the echo pulses. The predetermined direction is perpendicular to a direction of travel of the ultrasonic wave beam pulses.

In a second ultrasonic diagnostic apparatus of this invention, pulses of an ultrasonic wave beam are emitted into a body at a predetermined repetition period. Echo pulses of the ultrasonic wave beam are received via a plurality of different channels. Each of the received pulses is converted simultanenously into corresponding electric signals of the respective channels. A time-dependent change in a variation between the electric signals of the respective channels is derived. A component of a speed of moving matter within the body in a first predetermined direction is calculated on the basis of the derived time-dependent change. The moving matter causes the echo pulses. The first predetermined direction is perpendicular to a direction of travel of the ultrasonic wave beam pulses. A variation in phases of the electric signals is derived. An average value of the phase variation is calculated. A component of the speed of the moving matter in a second predetermined direction is calculated on the basis of the calculated average value of the phase variation. The second predetermined direction is parallel to the direction of the travel of the ultrasonic wave beam pulses.

BRIEF DESCRIPTION OF THE DRAWINGS

FIG. 18 is a block diagram of an ultrasonic diagnostic apparatus according to a tenth embodiment of this invention.

The same reference characters denote corresponding or like elements throughout the drawings.

DESCRIPTION OF THE FIRST PREFERRED EMBODIMENT

Figure 1:
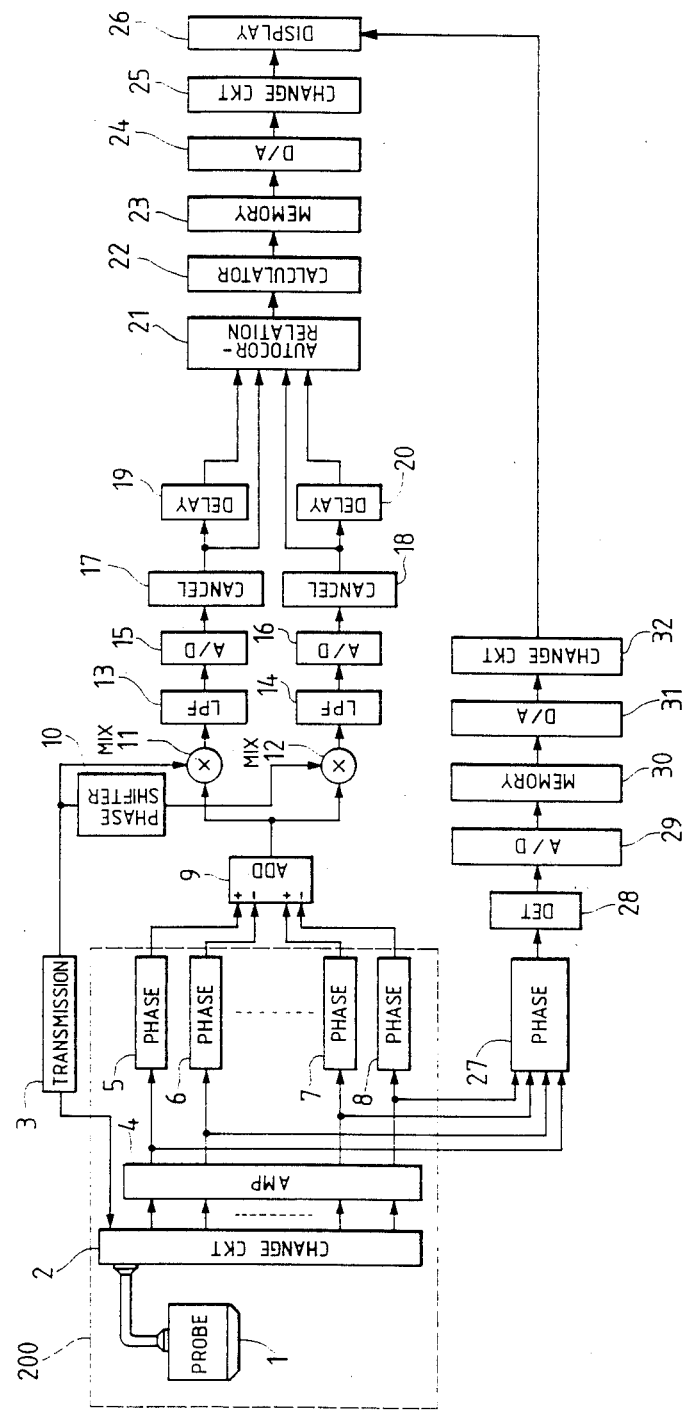
FIG. 1 is a block diagram of an ultrasonic diagnostic apparatus according to a first embodiment of this invention.
Figure 2:
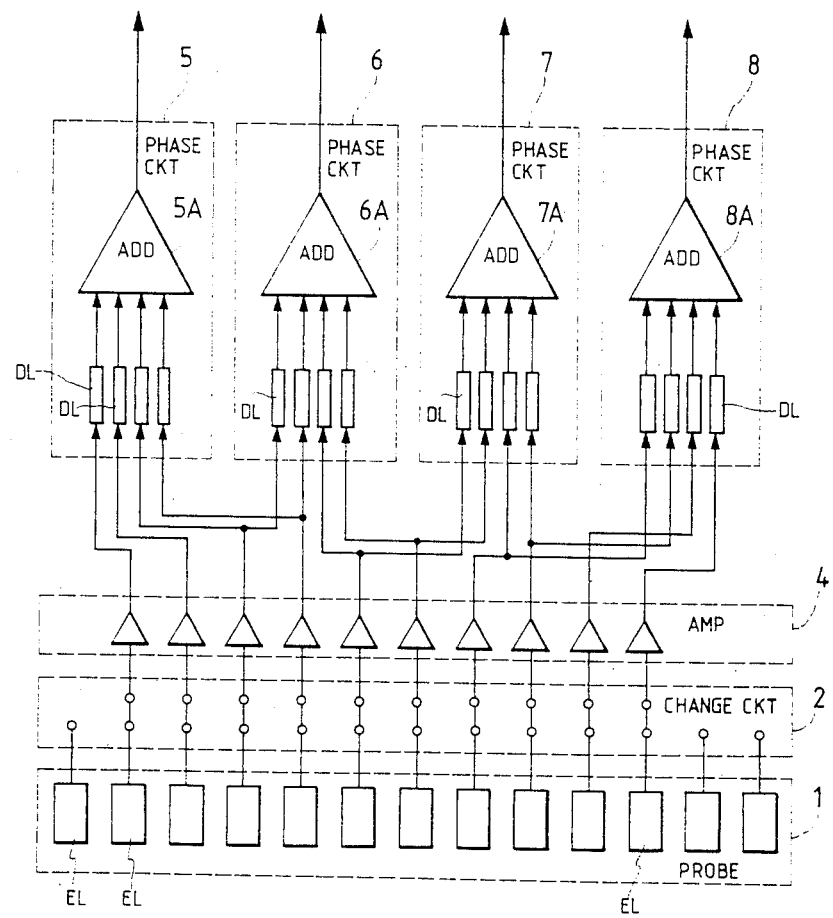
FIG. 2 is a block diagram of a parallel receiving circuit of the apparatus of FIG. 1.

With reference to FIGS. 1 and 2, an ultrasonic diagnostic apparatus includes an ultrasonic probe 1 having an in-line array of strip-shaped electro-acoustic transducer elements EL. The array of the transducer elements EL serves to emit a pulse beam of ultrasonic waves into a body (not shown). The transducer elements EL are connected to a change circuit 2.

In the embodiment of FIG. 2, during the transmission of ultrasonic wave beam pulses, the change circuit 2 sequentially selects ten of the transducer elements EL and connects a transmission circuit 3 to the selected transducer elements. Accordingly, ultrasonic wave beam pulses are simultaneously emitted from ten transducer elements. During the reception of echoes of ultrasonic wave beam pulses, the change circuit 2 selects four adjacent reception channels and connects the selected channels to reception amplifiers 4. Each channel is composed of four transducer elements.

The transmission circuit 3 generates electric transmission pulses driving the ultrasonic probe 1 and also adjusts the phases of the electric transmission pulses to control a pulse beam of ultrasonic waves emitted from the activated transducer elements.

Phasing circuits 5-8 control the reception directivity by adjusting the phases of received signals outputted from the respective transducer elements belonging to the activated reception channels. An adder 9 inverts alternate ones of received signals outputted from the phasing circuits 5-8, and sums the inverted signals and the remaining non-inverted received signals. An output signal from the adder 9 is applied to mixers 11 and 12.

The transmission circuit 3 outputs a first reference pulse signal to the mixer 11. The first reference pulse signal has a fixed timing relationship with the transmission pulses outputted from the transmission circuit 3. The frequency of the first reference pulse signal equals a given integer times the frequency of the transmission pulses. The device 11 mixes the output signal from the adder 9 and the first reference pulse signal. A phase shifter 10 changes the phase of the first reference pulse signal by 90° and thereby deriving a second reference pulse signal which is applied to the mixer 12. The device 12 mixes the output signal from the adder 9 and the second reference pulse signal.

A low pass filter 13 derives a first complex phase detection signal from an output signal of the mixer 11. The combination of the mixer 11 and the low pass filter 13 serves as a phase detector. An analog-to-digital converter 15 transforms the first phase detection signal into a corresponding first digital phase detection signal. The first digital phase detection signal is transmitted to a delay circuit 19 and an autocorrelator 21 via a canceler 17. The canceler 17 removes low frequency components from the first digital phase detection signal. An output signal from the delay circuit 19 is applied to the autocorrelator 21.

A low pass filter 14 derives a second complex phase detection signal from an output signal of the mixer 12. The combination of the mixer 12 and the low pass filter 14 serves as a phase detector. The second phase detection signal is a complex conjugate to the first phase detection signal. An analog-to-digital converter 16 transforms the second phase detection signal into a corresponding second digital phase detection signal. The second digital phase detection signal is transmitted to a delay circuit 20 and the autocorrelator 21 via a canceler 18. The canceler 18 removes low frequency components from the second digital phase detection signal. An output signal from the delay circuit 20 is applied to the autocorrelator 21.

The autocorrelator 21 calculates an autocorrelation function of a resultant of output signals from the cancelers 17 and 18 by using the output signals from the devices 17-20. A calculator 22 uses the autocorrelation function and thereby determines a component of a speed of moving liquid or portion within a body in a direction perpendicular to the direction of travel of the ultrasonic wave beam. An image or frame memory 23 temporarily holds an output signal from the calculator 22 which represents the calculated speed component. An output signal from the memory 23 is transformed by a digital-to-analog converter 24 into a corresponding analog video signal which is transmitted to a display 26 via a change circuit 25.

A phasing circuit 27 controls the phases of the received signals which are outputted from the reception amplifiers 4. A detector 28 derives a video signal from an output signal of the phasing circuit 27. The video signal is transformed by an analog-to-digital converter 29 into a corresponding digital signal which is temporarily stored in an image or frame memory 30. An output signal from the memory 30 is transformed by a digital-to-analog converter 31 into a corresponding analog video signal which is transmitted to the display 26 via a change circuit 32. The phasing circuit 27 is designed so that the display 26 can generate a B-scan mode image on the basis of the video signal fed via the change circuit 32.

More detailed description will follow. During the reception of ultrasonic wave beam pulses, ten transducer elements are simultaneously used in receiving echoes of ultrasonic wave beam pulses and they form four reception channels. Two transducer elements are allotted in common to a pair of adjacent reception channels. The output signals from the phasing circuits 5-8 correspond to the respective channels. The transducer elements which are selected by the change circuit 2 are connected to the corresponding reception amplifiers 4. In order to control the reception directivity, output signals from the reception amplifiers 4 are inputted into taps of delay circuits DL having delay times corresponding to the transducer elements in connection with the reception amplifiers respectively. Output signals from the delay circuits DL are transmitted to adders 5A-8A of the phasing circuits 5-8. In each of the four reception channels, the output signals from the delay circuits are summed by the adder. Pitches between adjacent reception channels correspond to distances between alternate transducer elements, so that it is possible to parallely obtain pieces of information which are spaced at intervals corresponding to two transducer elements and whose number equals the number of the activated reception channels. The ultrasonic probe 1, the change circuit 2, the amplifiers 4, and the phasing circuits 5-8 form a parallel receiving circuit 200.

During the transmission of ultrasonic wave beam pulses, all of the transducer elements which are connected to the simultaneously activated reception channels are connected to the transmission circuit 3. The transducer elements which are connected to the transmission circuit 3 emit a pulse beam of ultrasonic waves in response to electric transmission pulses fed from the transmission circuit 3. The transmission circuit 3 adjusts the phases of the transmission pulses, thereby controlling the directivity of the ultrasonic wave beam.

The first and second digital phase detection signals outputted from the A/D converters 15 and 16 have a complex conjugate relation with each other. The cancelers 17 and 18 remove low frequency components from the first and second digital phase detection signals. The removed low frequency components correspond to clutter components. The autocorrelator 21 calculates an autocorrelation function of a resultant of a pair of the complex phase detection signals on the basis of the delayed complex phase detection signals outputted from the delay circuits 19 and 20 and the non-delayed complex phase detection signals outputted from the cancelers 17 and 18.

The autocorrelation function is periodically calculated from complex phase detection signals derived at intervals which correspond to a repetition period T of ultrasonic wave beam pulses. A predetermined number "n" of ultrasonic wave beam pulses are generated to obtain data of each of points in a scanning line. Accordingly, a number of autocorrelation functions which corresponds to the predetermined number "n" are calculated for data of each points in a scanning line, and these autocorrelation functions are averaged to form a final autocorrelation function from which the data are derived. The predetermined number "n" is given by the following equation:

$$n \cdot T \cdot N \cdot F = 1 \tag{1}$$

where the character T denotes the repetition period of the ultrasonic wave beam pulses; the character N denotes a number of scanning lines forming a B-scan mode image; and the character F denotes a frame rate of the image or picture.

A variation $\theta$ in the phase of the autocorrelation function which occurs during the repetition period T of the ultrasonic wave beam pulses is given by the following equation:

$$\theta = \tan^{-1}(Si/Sr) \tag{2}$$

where the characters Si and Sr denote imaginary and real parts of the autocorrelation function respectively. The adder 9 is subjected to the received signals which result from the reflection of the ultrasonic wave beam at a moving liquid or portion within a body and which correspond to the respective channels spaced at equal pitches "p". In the adder 9, alternate ones of the received signals are inverted, and these inverted signals and the remaining non-inverted received signals are summed. The phase of the autocorrelation function varies in response to the speed of the moving liquid or portion within the body in a direction perpendicular to the direction of travel of the ultrasonic wave beam toward and into the moving liquid or portion within the body. Accordingly, the phase variation $\theta$ is given by the following equation:

$$\theta = (2\pi/p) \cdot V \cdot T \tag{3}$$

where the character V denotes the speed of the moving liquid or portion within the body in the direction perpendicular to the direction of travel of the ultrasonic wave beam, that is, in the direction parallel to the direction along which the reception channels are spaced or arranged. The calculator 22 determines the speed V of the moving liquid or portion by referring to the equations (2) and (3).

In summary, a speed of moving liquid or part of a body in a direction perpendicular to a direction of travel of an ultrasonic wave beam toward and into the moving liquid or part causes corresponding variations in received signals of the respective reception channels. These variations in the received signals are converted into a variation in an autocorrelation function. The variation in the autocorrelation fuction is used in calculating the speed of the moving liquid or part of the body in the direction perpendicular to the direction of travel of the ultrasonic wave beam, that is, in the direction parallel to a direction along which the reception channels or the transducer elements are spaced.

Figure 3:
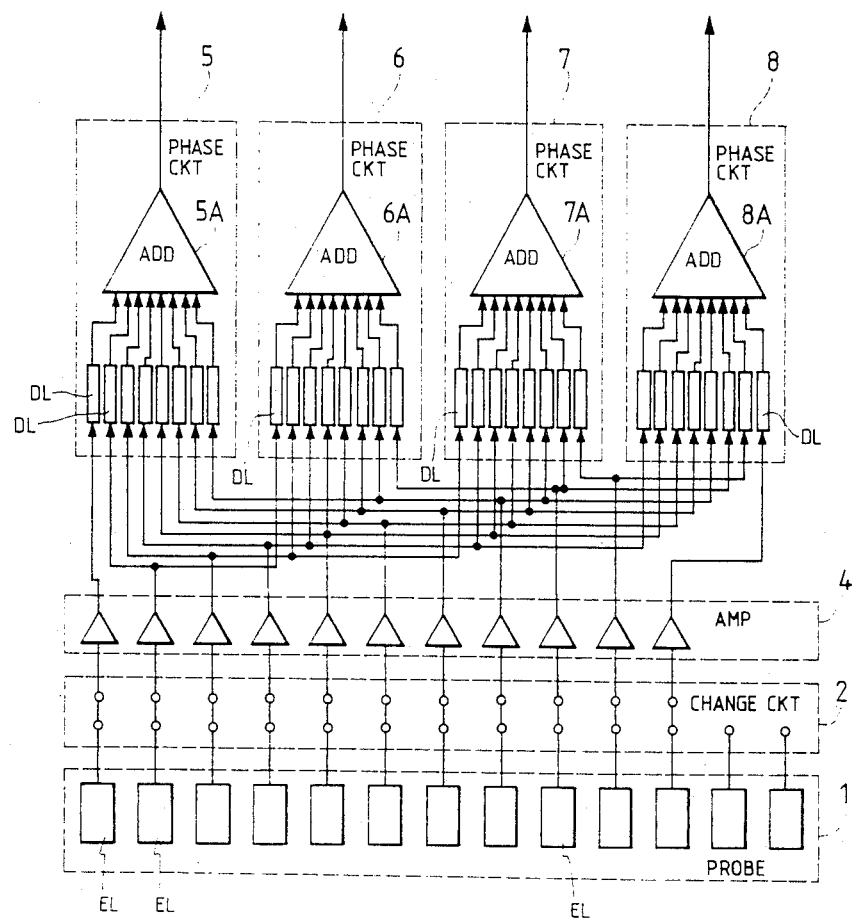
FIG. 3 is a block diagram of a modified parallel receiving circuit.

FIG. 3 shows a first modification of the embodiment of FIGS. 1 and 2. In the modification of FIG. 3: the number of simultaneously used reception channels is four; each channel is composed of eight transducer elements; and pitches between adjacent reception channels correspond to distances between adjacent transducer elements.

In a second modification of the embodiment of FIGS. 1 and 2, output signals from phasing circuits 5-8 are transmitted to an adder 9 via devices which weight the output signals from the phasing circuits 5-8. This weighting process is similar to a window process in general frequency analysis.

DESCRIPTION OF THE SECOND PREFERRED EMBODIMENT

Figure 4:
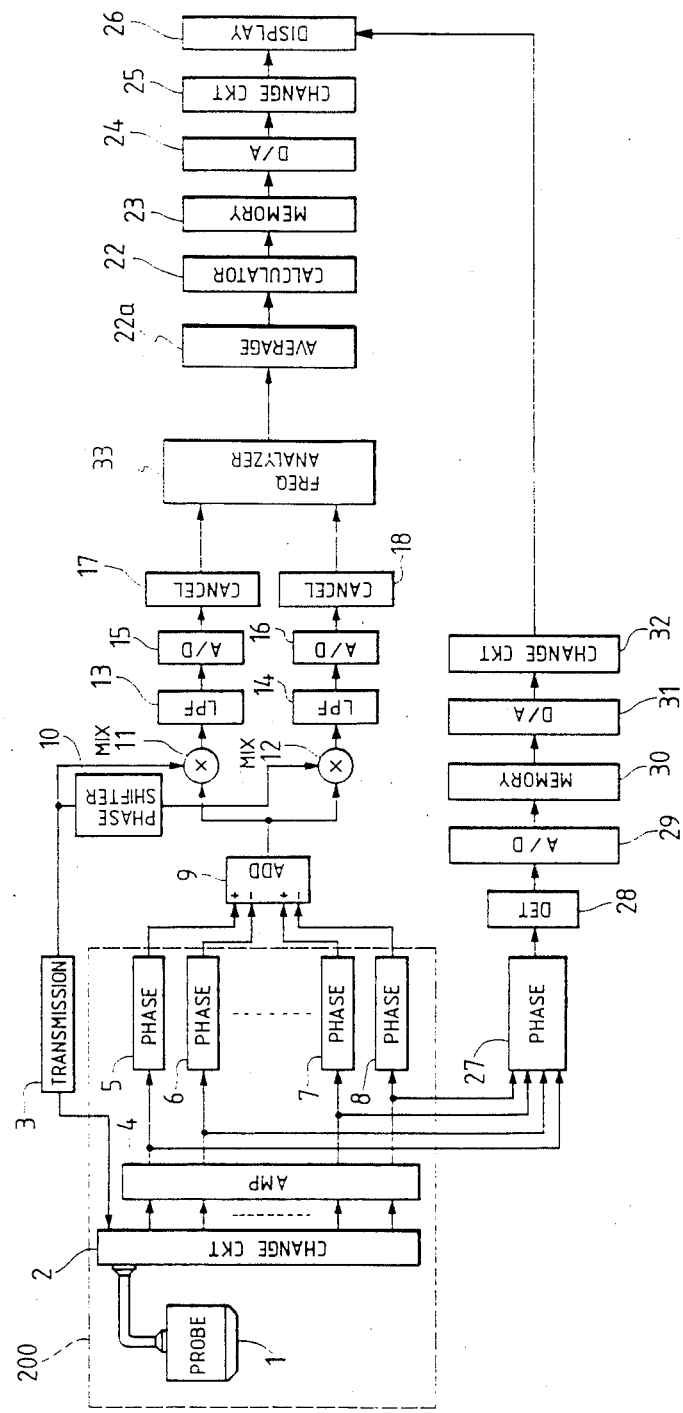
FIG. 4 is a block diagram of an ultrasonic diagnostic apparatus according to a second embodiment of this invention.

FIG. 4 shows a second embodiment of this invention which is similar to the embodiment of FIGS. 1 and 2 except for design changes indicated hereinafter.

In the embodiment of FIG. 4, first and second complex phase detection signals outputted from cancelers 17 and 18 are applied to a frequency analyzer 33 which detects a spectrum of a resultant of the first and second complex phase detection signals. An averaging circuit 22a calculates an average value of the detected spectrum. A calculator 22 uses the calculated average value in determining a speed of moving liquid or part of a body in a direction perpendicular to a direction of travel of an ultrasonic wave beam toward and into the moving liquid or part.

Figure 5:
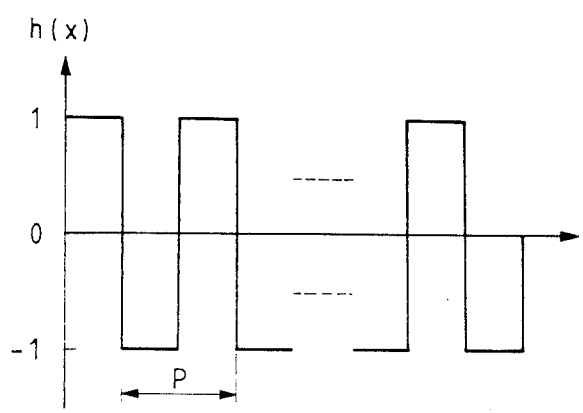
FIGS. 5 and 6 are diagrams showing characteristics of the adder of FIG. 4.

The following characters are introduced to represent various functions. The character f(x) denotes received signals in respective reception channels which depend on the motion of moving liquid or part of a body. The character h(x) denotes a function corresponding to operation of an adder 9 in which alternate ones of the received signals are inverted and in which the inverted signals and the non-inverted received signals are summed. As shown in FIG. 5, the function h(x) varies in a rectangular wave having a period corresponding to a pitch "p" between the reception channels. The character g(x) denotes a resultant received sigal which is derived by the summing process in the adder 9. The character $G(\omega)$ denotes Fourier transform of the function g(x). The character H(k) denotes Fourier transform of the function h(x). The character F(k) denotes Fourier transform of the function f(x).

Figure 6:
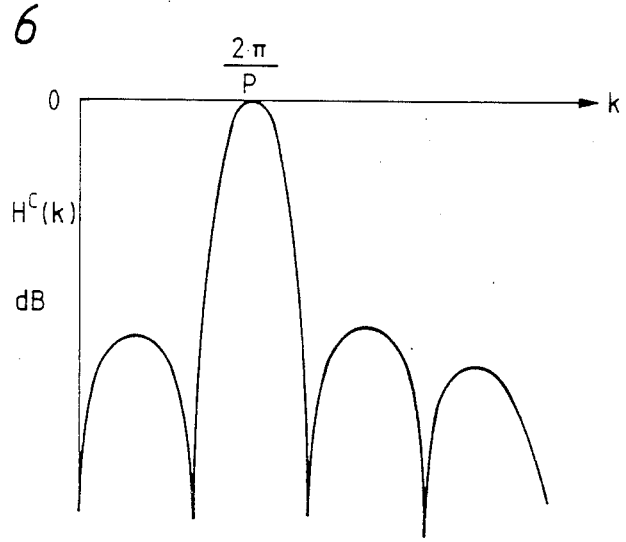

The functions G, H, and F have a relationship as follows:

$$G(\omega) = (1/V) \cdot H^c(\omega/V) \cdot F(\omega/V) \tag{4}$$

where the character V denotes a speed of moving liquid or part of a body in a direction perpendicular to a direction of travel of an ultrasonic wave beam toward and into the moving liquid or part, and where the character $H^c$ denotes a complex conjugate to the function H. As shown in FIG. 6, the function $H^c(k)$ shows a sharp peak at the value "k" equal to "$2\pi/p$" where the character "p" denotes the pitch between the reception channels. The function F(k) is broad and varies gradually. Since the function $G(\omega)$ is a product of the functions H and F, the function $G(\omega)$ has a sharp peak.

The frequency analyzer 33 determines a frequency spectrum on the basis of complex phase detection signals derived at intervals which correspond to a repetition period T of ultrasonic wave beam pulses. A predetermined number "i" of ultrasonic wave beam pulses are generated to obtain data of each of points in a scanning line. Accordingly, a number of spectrums which corresponds to the predetermined number "i" are determined for data of each of points in a scanning line, and the spectrums are averaged to obtain a final spectrum from which the data are derived. The predetermined number "i" is given by the following equation:

$$i \cdot T \cdot N \cdot F = 1 \tag{5}$$

where the character T denotes the repetition period of the ultrasonic wave beam pulses; the character N denotes a number of scanning lines forming a B-scan mode image; and the character F denotes a frame rate of the image or picture.

The averaging circuit 22a determines an average value ωp by using the frequency spectrum which is derived by the frequency analyzer 33. The average value ωp gives a peak of the frequency spectrum. Since the number "i" is limited to ensure real-time characteristics of the generation of images and thus the frequency resolution is low, the average value ωp is determined in a frequency spectrum moment as follows:

$$\omega p = \int \omega \cdot |G(\omega)| \tag{6}$$

The calculator 22 determines a speed V of moving liquid or part of a body in a direction perpendicular to a direction of travel of an ultrasonic wave beam by referring to the following equation:

$$V = (\omega p \cdot p)/2\pi \tag{7}$$

In summary, a speed of moving liquid or part of a body in a direction perpendicular to a direction of travel of an ultrasonic wave beam toward and into the moving liquid or part causes corresponding variations in received signals of the respective reception channels. These variations in the received signals are represented by a frequency spectrum which is derived by the frequency analyzer 33. An average value of the frequency spectrum is calculated by the averaging circuit 22a. The calculator 22 uses the average value of the frequency spectrum in determining the speed of the moving liquid or part of the body in the direction perpendicular to the direction of travel of the ultrasonic wave beam, that is, in the direction parallel to a direction along which the reception channels or the transducer elements are spaced.

In a modification of the embodiment of FIGS. 4-6, output signals from phasing ircuits 5-8 are transmitted to an adder 9 via a device which weights the output signals from the phasing circuits 5-8. This weighting process is similar to a window process in general frequency analysis.

DESCRIPTION OF THE THIRD PREFERRED EMBODIMENT

Figure 7:
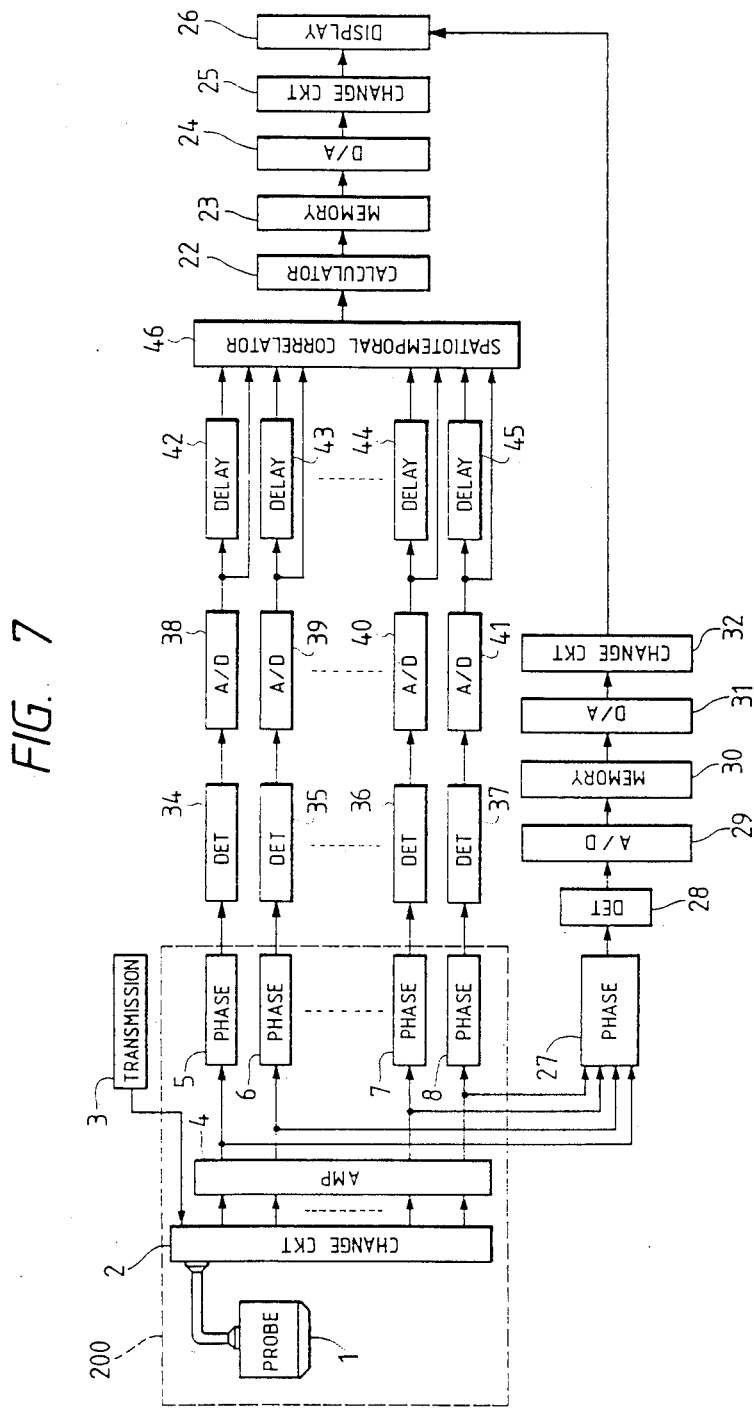
FIG. 7 is a block diagram of an ultrasonic diagnostic apparatus according to a third embodiment of this invention.

FIG. 7 shows a third embodiment of this invention which is similar to the embodiment of FIGS. 1-3 except for design changes indicated hereinafter.

In the embodiment of FIG. 7, received signals of respective reception channels which are outputted from phasing circuits 5-8 are detected by detectors 34-37 respectively. Output signals from the detectors 34-37 are transformed by analog-to-digital converters 38-41 into corresponding digital signals respectively. Output signals from the A/D converters 38-41 are directly applied to a spatiotemporal correlator 46. Output signals from the A/D converters 38-41 are also applied to the spatiotemporal correlator 46 via respective delay circuits 42-45. Delay times T determined by the delay circuits 42-45 are chosen to equal a repetition period T of ultrasonic wave beam pulses.

The spatiotemporal correlator 46 calculates a spatiotemporal correlation function between the reception channels in a period T at intervals which correspond to two transducer elements for the arrangement of FIG. 2 and which correspond to one transducer element for the arrangement of FIG. 3. The spatiotemporal correlation function is determined on the basis of a combination of the digital delayed received signals and the digital non-delayed received sigals of the respective reception channels which are outputted from the delay circuits 42-45 and the A/D converters 38-41.

Figure 8:
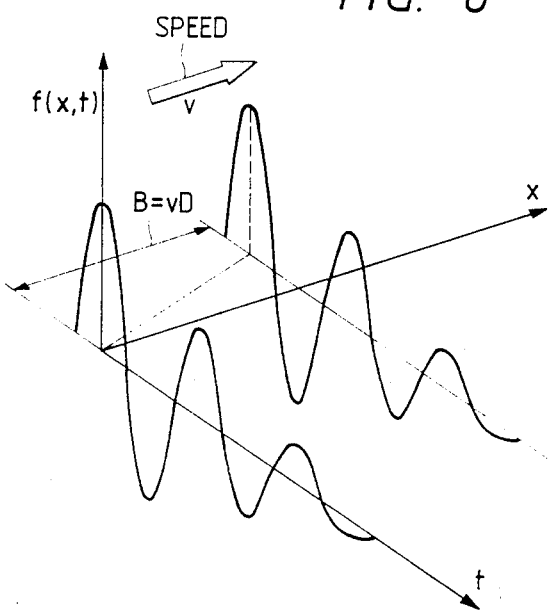
FIG. 8 is a diagram showing the relationship between phases of received signals of adjacent channels in the apparatus of FIG. 7.

It is thought that the reflection of an ultrasonic wave beam at moving liquid or part of a body cuases only a small change between received signals of adjacent reception channels. As shown in FIG. 8, received signals of channels spaced by a distance B have phases different from each other by a time D. The time D is given by the following equation:

$$D = B/v \tag{8}$$

where the character "v" denotes a component of a speed of the moving liquid or part in a direction perpendicular to a direction of travel of an ultrasonic wave beam toward and into the moving liquid or part.

Figure 9:
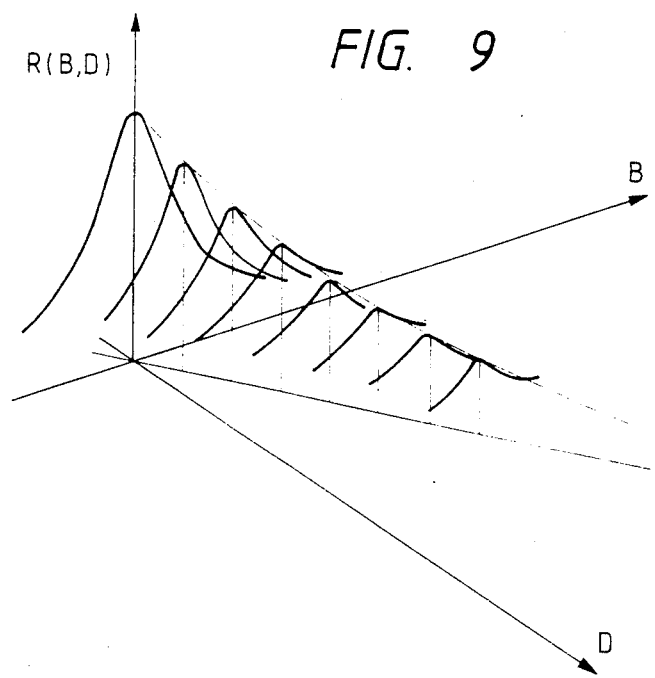
FIG. 9 is a diagram showing a distribution of spatio-temporal functions in the apparatus of FIG. 7.

A component of the speed of the moving liquid or part in a direction parallel to a direction of travel of the ultrasonic wave beam would cause further phase shifts in the received signals due to Doppler effect. To remove such an adverse phenomenon, the detectors 34-37 extract envelopes from the received signals which are outputted from the phasing circuit 5-8. Accordingly, as shown in FIG. 9, the spatiotemporal correlation function R peaks at the distance B equal to a value Bp. The value Bp is given by the following equation:

$$Bp = v \cdot D \tag{9}$$

To obtain data of each of points in a scanning line, the spatiotemporal correlation function is periodically calculated a predermined number "a" of times at intervals T, and the calculated spatiotemporal correlation functions are averaged to determine a final spatiotemporal correlation function. The predetermined number "a" is given by the following equation:

$$a \cdot T \cdot N \cdot F = 1 \tag{10}$$

where the character T denotes the repetition period of the ultrasonic wave beam pulses; the character N denotes a number of scanning lines forming a B-scan mode image; and the character F denotes a frame rate of the image or picture.

An output signal from the spatiotemporal correlator 46 which represents the final spatiotemporal correlation function is applied to a calculator 22. The equation (9) is transformed into the following equation:

$$v = Bp/D \tag{11}$$

The calculator 22 determines the speed "v" of moving liquid or part of a body in a direction perpendicular to a direction of travel of the ultrasonic wave beam by referring to the equation (11).

As understood from the previous description, the spatial point at which the spatiotemporal correlation function peaks shifts in proportion to the speed of the moving liquid or part of the body in the direction perpendicular to the direction of travel of the ultrasonic wave beam. Therefore, it is possible to accurately calculate the speed of the moving liquid or part in the direction perpendicular to the direction of travel of the ultrasonic wave beam.

In a first modification of the embodiment of FIGS. 7-10, the detectors 34-37 are replaced with a digital signal processor connected to the A/D converters 38-41 and having a function of detection.

In a second modification of the embodiment of FIGS. 7-10, the detectors 34-37 and the A/D converters 38-41 are replaced with an arrangement where A/D converters are incorpolated into the phasing circuits 5-8 and where a digital signal processor has functions of phasing and detection.

DESCRIPTION OF THE FOURTH PREFERRED EMBODIMENT

Figure 10:
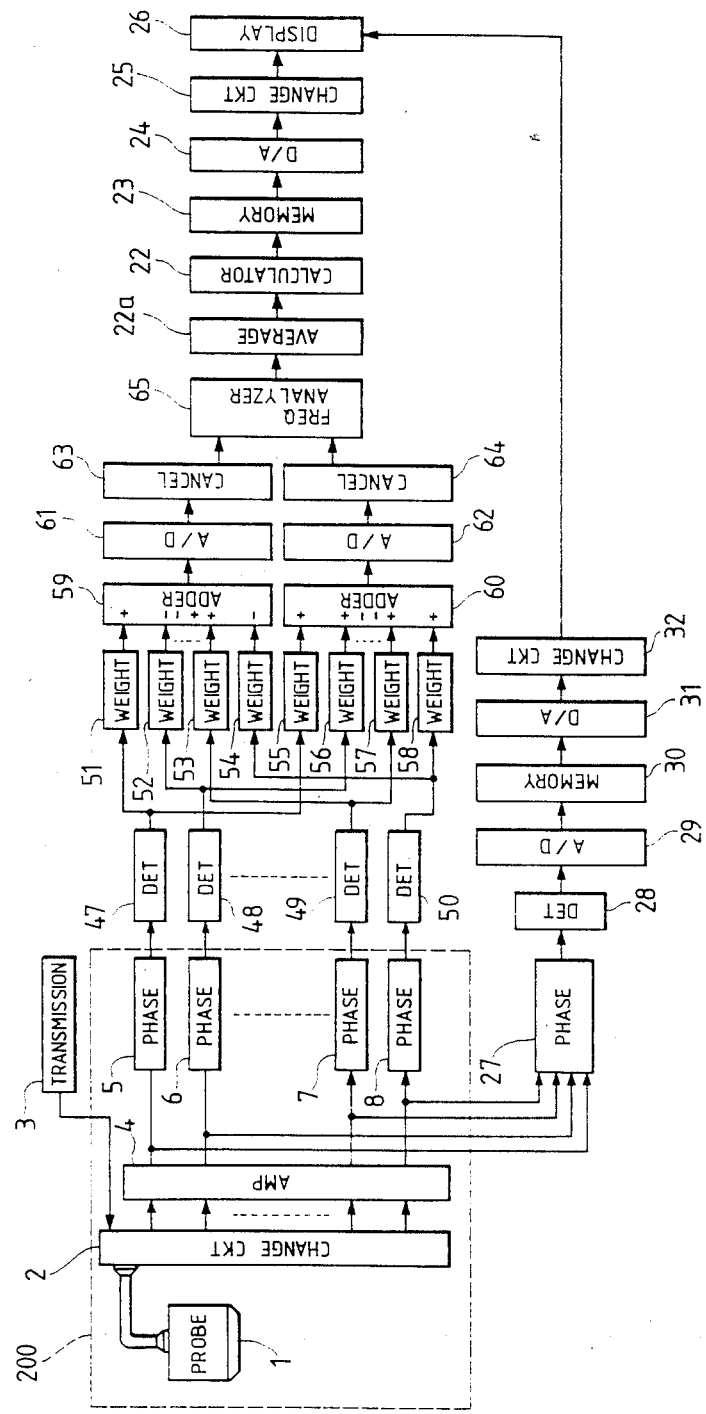
FIG. 10 is a block diagram of an ultrasonic diagnostic apparatus according to a fourth embodiment of this invention.

FIG. 10 shows a fourth embodiment of this invention which is similar to the embodiment of FIGS. 4-6 except for design changes described hereinafter.

In the embodiment of FIG. 10, received signals outputted from phasing circuits 5-8 are detected by detectors 47-50 respectively. Detected signals outputted from the detectors 47-50 are transmitted to adders 59 and 60 via weighting devices 51-58. The weighting process performed by the devices 51-58 is similar to a window process in general frequency analysis and serves to suppress a side lobe of a frequency spectrum in a spatial frequency range.

The adders 59 and 60 sums output received signals from the weighting devices 51-58 in such a manner that the signs of alternate groups are inverted, each group being composed of the received signals of adjacent two reception channels. The ways of the sign changes in the adders 59 and 60 are shifted from each other by a quantity corresponding to one reception channel. This design allows the adders 59 and 60 to output complex detection signals having phases different from each other by 90°.

The complex detection signals which are outputted from the adders 59 and 60 are transformed by analog-to-digital converters 61 and 62 into corresponding digital complex detection signals respectively. The digital complex detection signals are transmitted from the A/D converters 61 and 62 to a frequency analyzer 65 via cancelers 63 and 64 respectively. The cancelers 63 and 64 removes clutter components from the digital complex detection signals.

Figure 11:
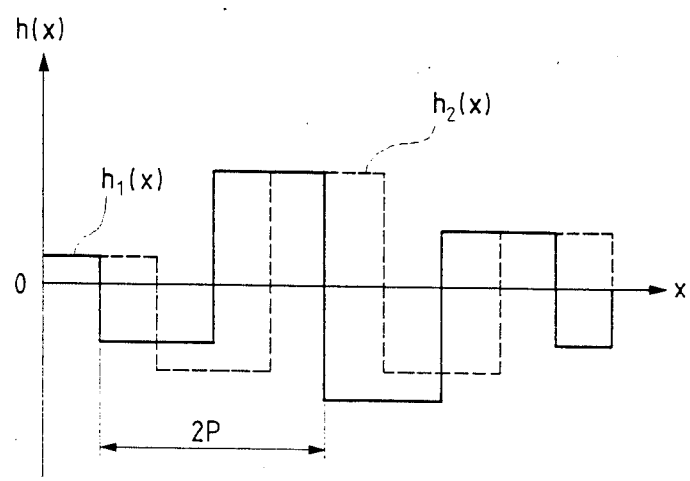
FIGS. 11 and 12 are diagrams showing characteristics of the adders of FIG. 10.
Figure 12:
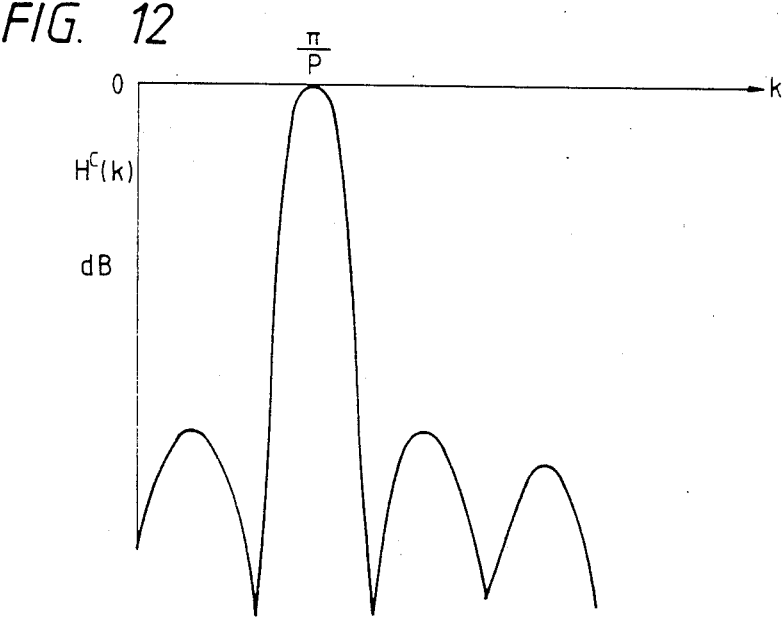

The frequency analyzer 65 calculates a frequency spectrum of the complex detection signals in a way basically similar to the way of calculating a frequency spectrum in the embodiment of FIGS. 4-6. In the embodiment of FIG. 10, as shown in FIG. 11, a complex function h(x) varies in a rectangular wave having a period corresponding to twice a pitch "p" between the reception channels. In FIG. 11, the characters h1(x) and h2(x) denote real part and imaginary part of the function h(x). In addition, as shown in FIG. 12, a function $H^c(k)$ shows a sharp peak at a value "k" equal to "$\pi/p$" where the character "p" denotes the pitch between the reception channels.

A calculator 22 connected to the frequency analyzer 65 determines a speed V of moving liquid or part of a body in a direction perpendicular to a direction of travel of an ultrasonic wave beam by referring to the following equation:

$$V = (\omega p \cdot p)/\pi \quad (12)$$

The equation (12) corresponds to the equation (7) in the embodiment of FIGS. 4-6.

A modification of the embodiment of FIGS. 10-12 additionally includes an arrangement detecting a component of a speed of moving liquid or part in a direction parallel to a direction of travel of an ultrasonic wave beam. This arrangement allows a display indication of a vector speed of the moving liquid or part. Such an arrangement is similar to corresponding arrangements in fifth to tenth embodiments of this invention which will be described hereinafter.

DESCRIPTION OF THE FIFTH PREFERRED EMBODIMENT

Figure 13:
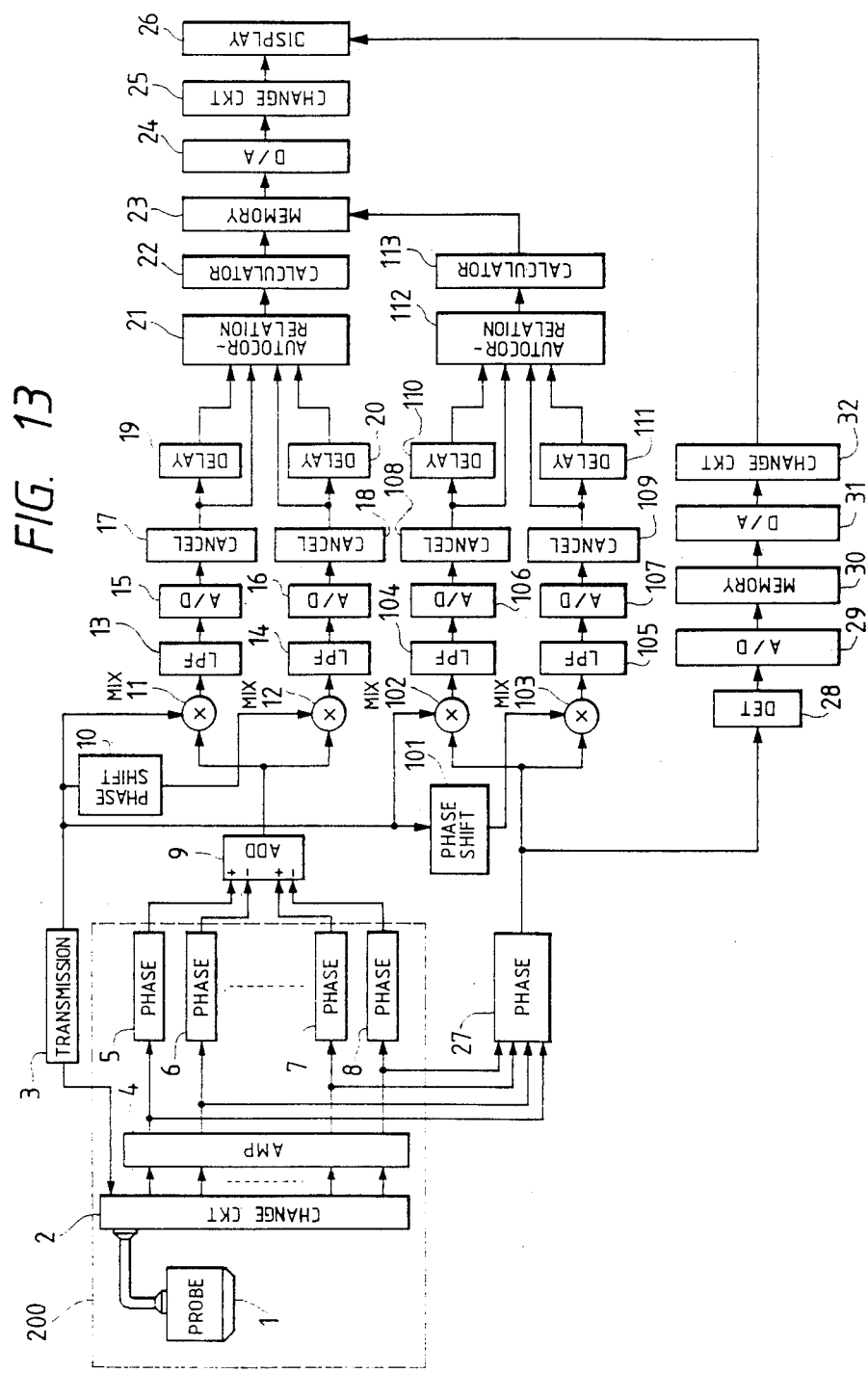
FIG. 13 is a block diagram of an ultrasonic diagnostic apparatus according to a fifth embodiment of this invention.

FIG. 13 shows a fifth embodiment of this invention which is similar to the embodiment of FIGS. 1-3 except for design changes described hereinafter.

The embodiment of FIG. 13 additionally includes a combination of a phase shifter 101, mixers 102 and 103, low pass filters 104 and 105, analog-to-digital converters 106 and 107, cancelers 108 and 109, delay circuits 110 and 111, an autocorrelator 112, and a calculator 113 which is similar to a combination of devices 10-22. A first reference pulse signal outputted from a transmission circuit 3 is applied to the phase shifter 101 and the mixer 102. The phase shifter 101 changes a phase of the first reference pulse signal by 90° and thereby deriving a second reference pulse signal which is applied to the mixer 103. An output signal from a phasing circuit 27 is applied to the mixers 102 and 103. An output signal from the calculator 113 is stored into a memory 23.

The device 102 mixes the output signal from the phasing circuit 27 and the first reference pulse signal. The device 103 mixes the output signal from the phasing circuit 27 and the second reference pulse signal.

The low pass filter 104 derives a first phase detection signal from an output signal of the mixer 102. The A/D converter 106 transforms the first phase detection signal into a corresponding first digital phase detection signal. The first digital phase detection signal is transmitted to the delay circuit 110 and the autocorrelator 112 via the canceler 108. The canceler 108 removes low frequency clutter components from the first digital phase detection signal. An output signal from the delay circuit 110 is applied to the autocorrelator 113.

The low pass filter 105 derives a second phase detection signal from an output signal of the mixer 103. The A/D converter 107 transforms the second phase detection signal into a corresponding second digital phase detection signal. The second digital phase detection signal is transmitted to the delay circuit 111 and the autocorrelator 112 via the canceler 109. The canceler 109 removes low frequency clutter components from the second digital phase detection signal. An output signal from the delay circuit 111 is applied to the autocorrelator 112.

The autocorrelator 112 calculates an autocorrelation function of a resultant of complex phase detection signals on the basis of output signals from the devices 108-111. The calculator 113 determines a component of a speed of moving liquid or part of a body in a direction parallel to a direction of travel of an ultrasonic wave beam. The image or frame memory 23 temporarily holds an output signal from the calculator 113 which represents the calculated speed component.

The first and second digital phase detection signals outputted from the A/D converters 106 and 107 have a complex conjugate relation with each other. The autocorrelator 112 calculates an autocorrelation function of the complex phase detection signals on the basis of the delayed complex phase detection signals outputted from the delay circuits 110 and 111 and the non-delayed complex phase detection signals outputted from the cancelers 108 and 109.

The characters Cr and Ci are now introduced to represent real part and imaginary part of the autocorrelation function. A frequency shift "fd" due to Doppler effect has the following relationship with the parameters Cr and Ci:

$$fd = (\tfrac{1}{2}\pi T) \cdot \tan^{-1}(Ci/Cr) \tag{13}$$

where the character T denotes a repetition period of ultrasonic wave beam pulses. Doppler effect causes a frequency shift of the ultrasonic wave beam which varies with a component of a speed of moving liquid or part of a body in a direction parallel to a direction of travel of the ultrasonic wave beam. Firstly, the calculator 113 determines the frequency shift "fd" on the basis of the autocorrelation function by referring to the equation (13). Secondly, the calculator 113 uses the frequency shift "fd" in determining the component of the speed in the direction parallel to the direction of the travel of the ultrasonic wave beam.

As understood from the previous description, it is possible to measure both components of a speed of moving liquid or part in directions perpendicular and parallel to the direction of the travel of the ultrasonic wave beam toward and into the moving liquid or part. Accordingly, the display 26 indicates a vector speed of the moving liquid or part.

In a modification of the embodiment of FIG. 13, output signals from phasing circuits 5-8 are transmitted to an adder 9 via devices which weight the output signals from the phasing circuits 5-8. This weighting process is similar to a window process in general frequency analysis.

DESCRIPTION OF THE SIXTH PREFERRED EMBODIMENT

Figure 14:
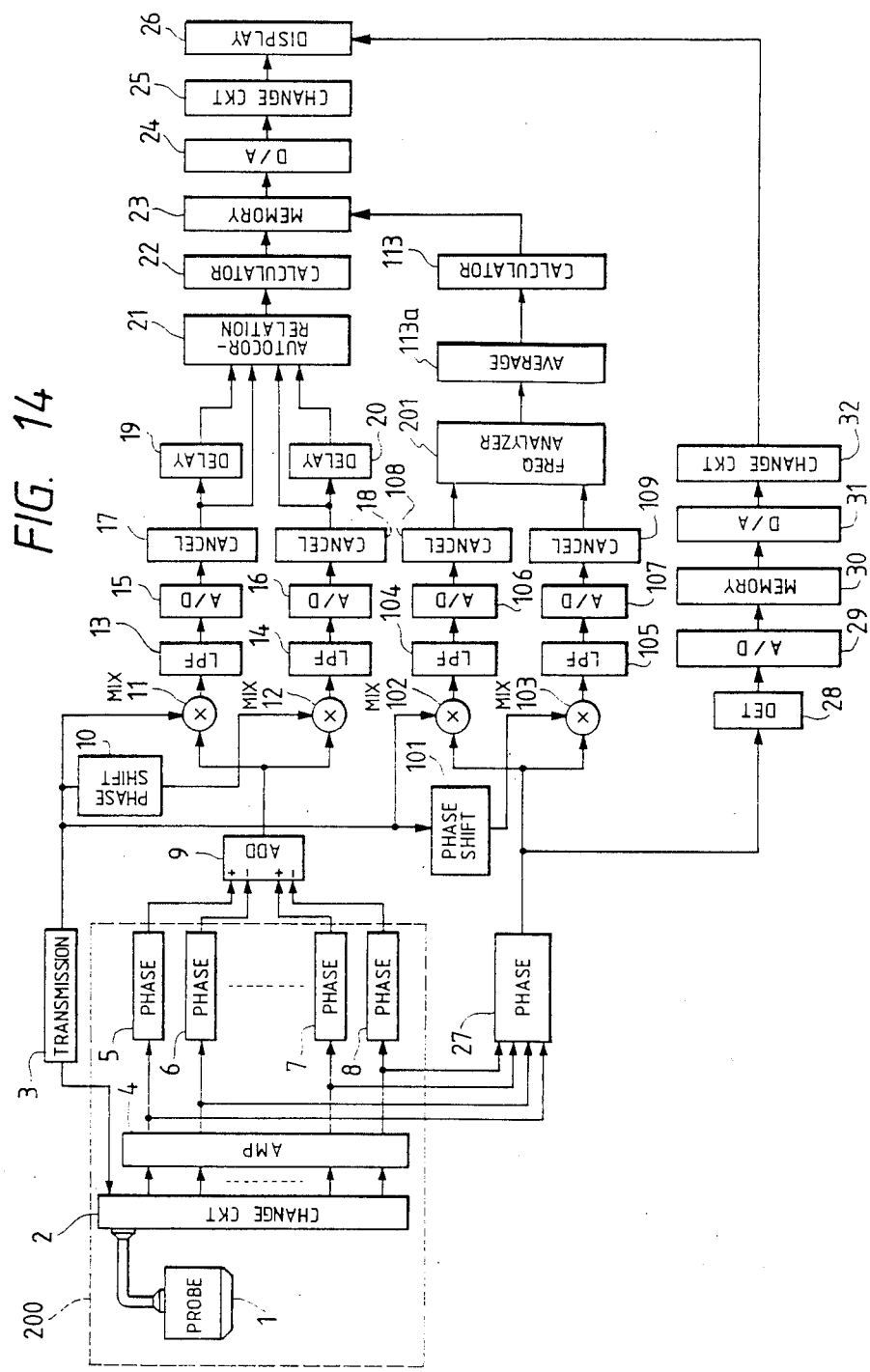
FIG. 14 is a block diagram of an ultrasonic diagnostic apparatus according to a sixth embodiment of this invention.

FIG. 14 shows a sixth embodiment of this invention which is similar to the embodiment of FIG. 13 except for the following design changes.

In the embodiment of FIG. 14, a combination of a frequency analyzer 201 and an averaging circuit 113a replaces a combination of devices 110-112 (see FIG. 13). The frequency analyzer 201 periodically determines a frequency spectrum of complex phase detection signals outputted from canclers 108 and 109. The averaging circuit 113a periodically calculates an average value of the determined frequency spectrum. A calculator 113 determines a variation in the average value of the frequency spectrum and directly calculates a Doppler-effect frequency shift from the determined variation in the average value of the frequency spectrum. The calcuator 113 uses the calculated frequency shift in determining a component of a speed of moving liquid or part in a direction parallel to a direction of travel of an ultrasonic wave beam.

DESCRIPTION OF THE SEVENTH PREFERRED EMBODIMENT

Figure 15:
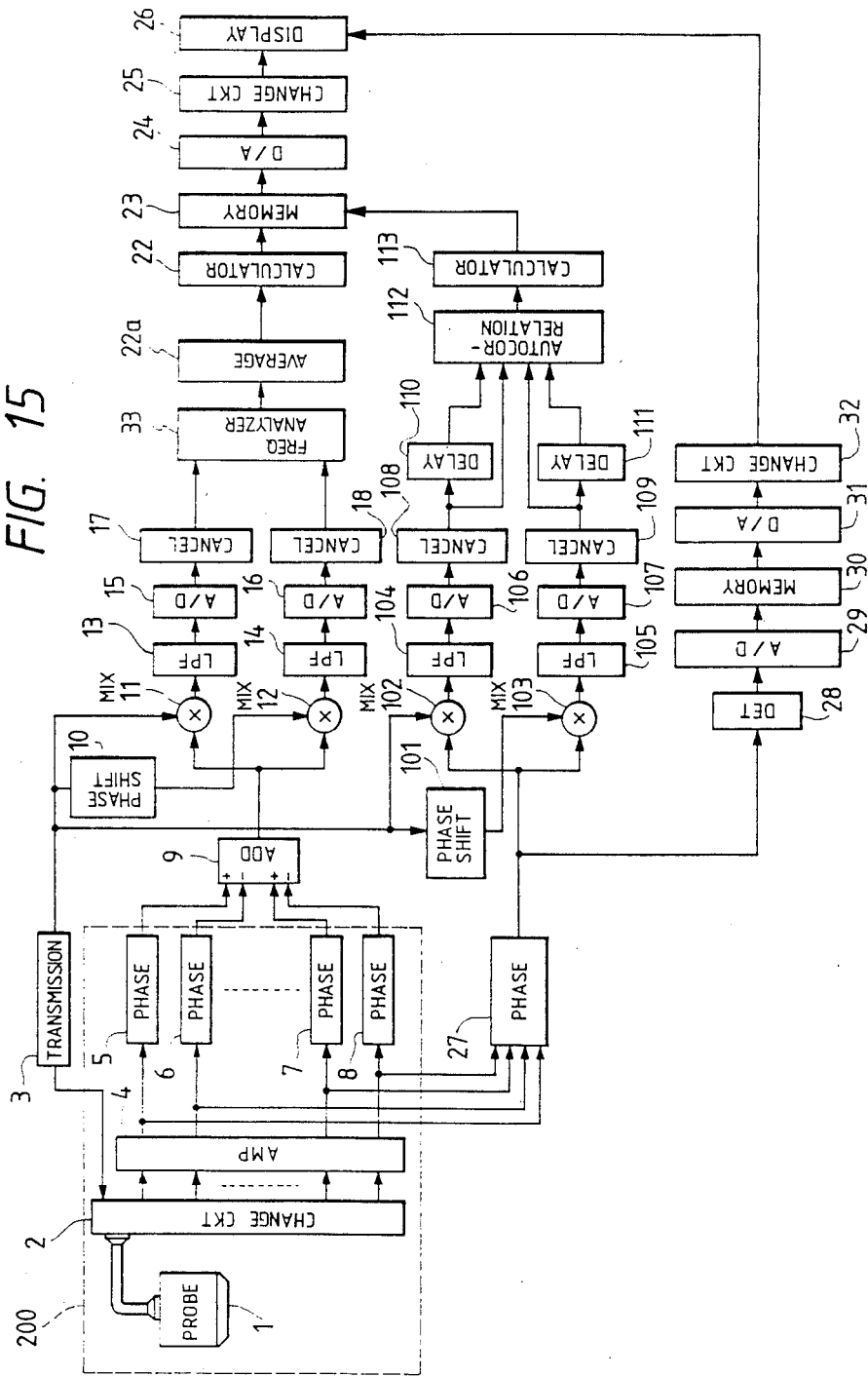
FIG. 15 is a block diagram of an ultrasonic diagnostic apparatus according to a seventh embodiment of this invention.

FIG. 15 shows a seventh embodiment of this invention which is similar to the embodiment of FIG. 13 except for the following design changes.

In the embodiment of FIG. 15, a combination of a frequency analyzer 33 and an averaging circuit 22a replaces a combination of devices 19-21 (see FIG. 13). The arrangement composed of the frequency analyzer 33 and the averaging circuit 22a is similar to the corresponding arrangement of FIG. 4.

DESCRIPTION OF THE EIGHTH PREFERRED EMBODIMENT

Figure 16:
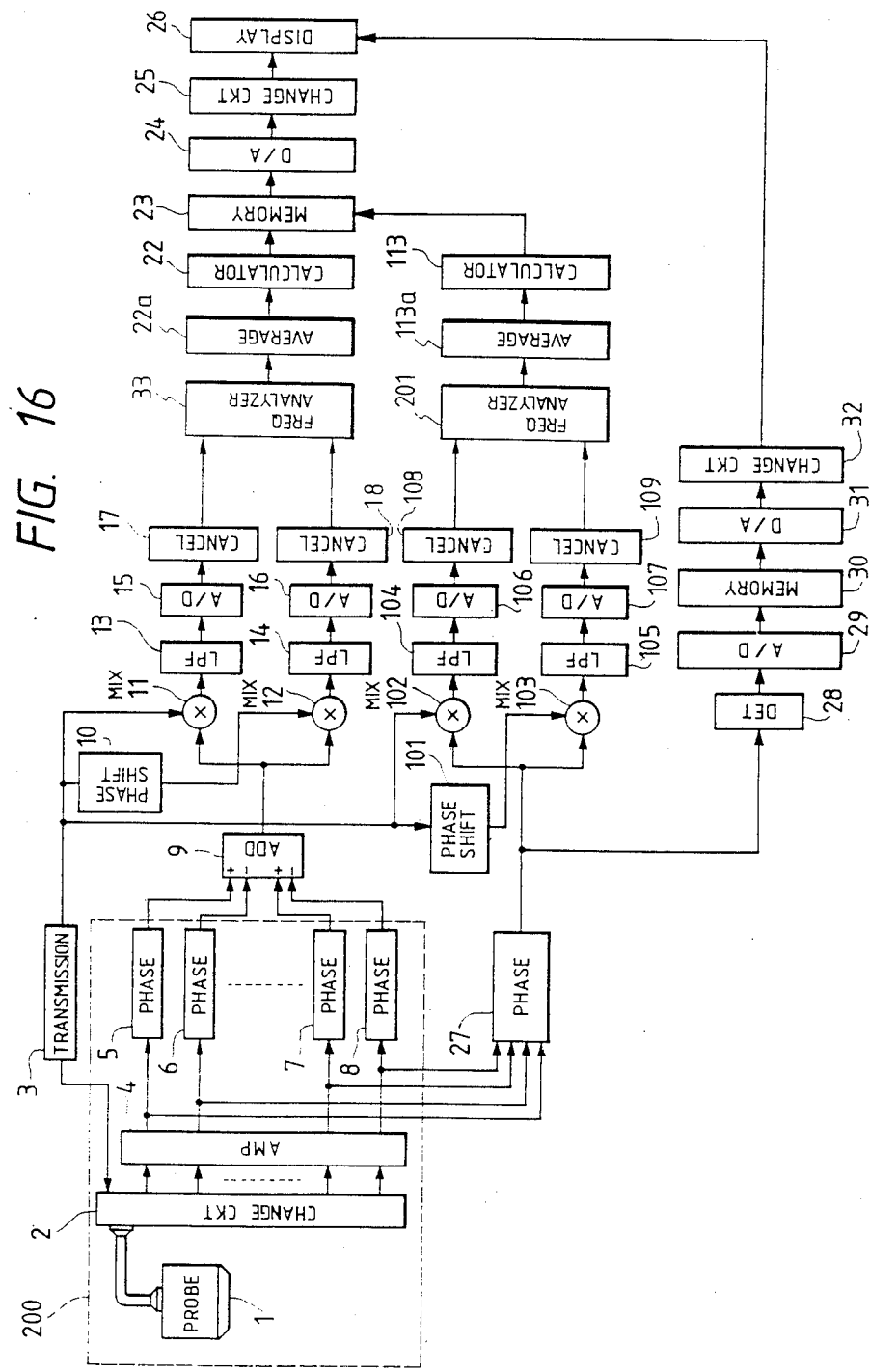
FIG. 16 is a block diagram of an ultrasonic diagnostic apparatus according to an eighth embodiment of this invention.

FIG. 16 shows an eighth embodiment of this invention which is similar to the embodiment of FIG. 15 except for the following design change.

In the embodiment of FIG. 16, a combination of a frequency analyzer 201 and an averaging circuit 113a replaces a combination of devices 110-112 (see FIG. 15). The arrangement composed of the frequency analyzer 201 and the averaging circuit 113a is similar to the corresponding arrangement of FIG. 14.

DESCRIPTION OF THE NINTH PREFERRED EMBODIMENT

Figure 17:
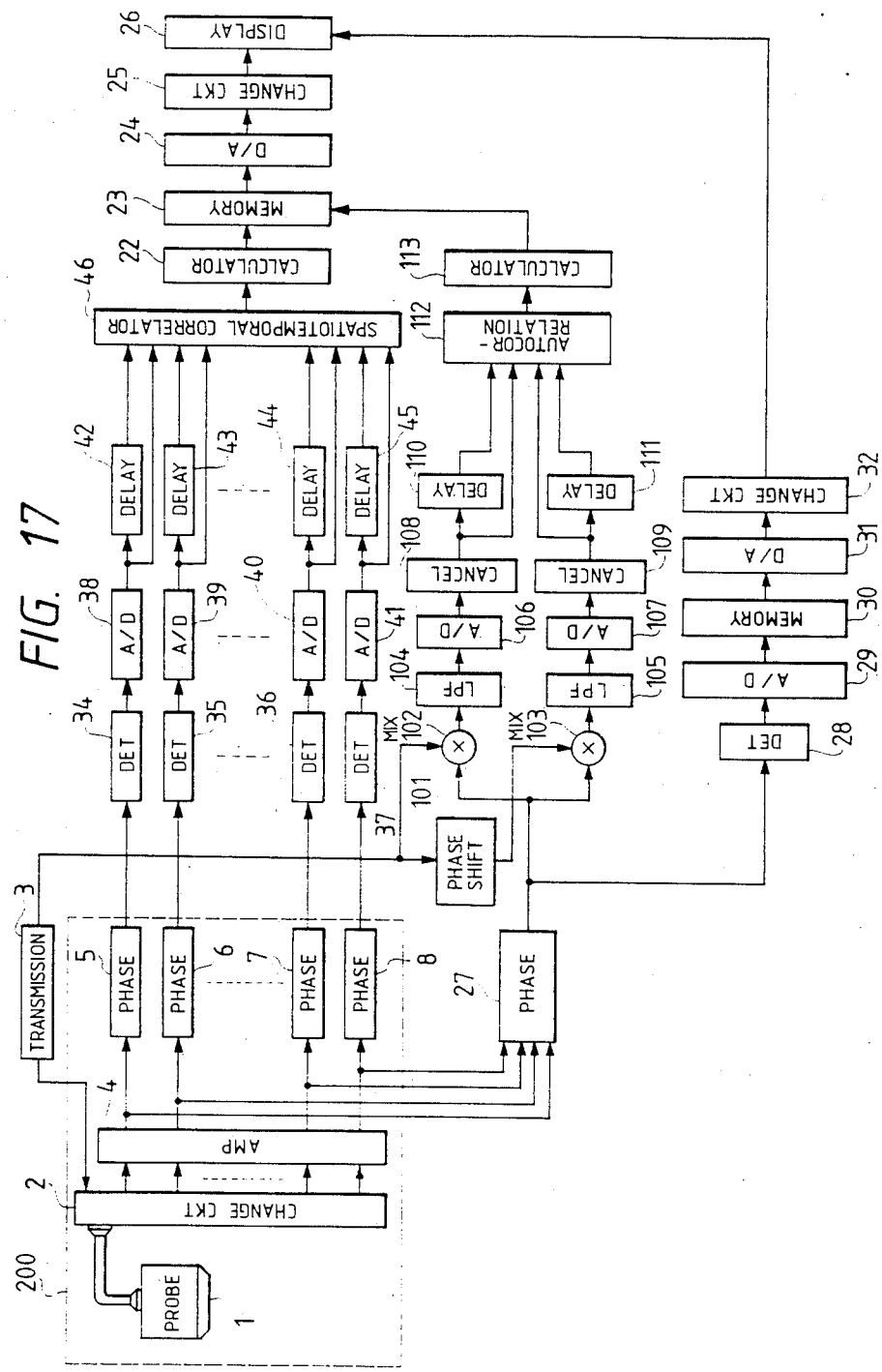
FIG. 17 is a block diagram of an ultrasonic diagnostic apparatus according to a ninth embodiment of this invention.

FIG. 17 shows a ninth embodiment of this invention which is similar to the embodiment of FIG. 13 except for the following design change.

In the embodiment of FIG. 17, a combination of detectors 34-37, analog-to-digital converters 38-41, delay circuits 42-45, and a spatiotemporal correlator 46 replaces a combination of devices 10-21 (see FIG. 13). The arrangement composed of the devices 34-46 is similar to the corresponding arrangement of FIG. 7.

DESCRIPTION OF THE TENTH PREFERRED EMBODIMENT

FIG. 18 shows a tenth embodiment of this invention which is similar to the embodiment of FIG. 17 except for the following design change.

In the embodiment of FIG. 18, a combination of a frequency analyzer 201 and an averaging circuit 113a replaces a combination of devices 110-112 (see FIG. 17). The arrangement composed of the frequency analyzer 201 and the averaging circuit 113a is similar to the corresponding arrangement of FIG. 14.

What is claimed is:

1. An ultrasonic diagnostic apparatus comprising:
   (a) means for emitting pulses of an ultrasonic wave beam into a body at a predetermiend repetition period;
   (b) means for receiving echo pulses of the ultrasonic wave beam via a plurality of different channels, and for simultaneously converting each of the received pulses into corresponding electric signals of the respective channels;
   (c) deriving means for deriving a time-dependent change in a variation between the electric signals of the respective channels; and
   (d) component calculating means for calculating a component of a speed of moving matter within the body in a predetermined direction on the basis of the derived time-dependent change, wherein the moving matter causes the echo pulses and wherein the predetermiend direction is perpdendicular to a direction of travel of the ultrasonic wave beam pulses,
wherein said deriving means comprises spatial filter means for detecting a condition of the variaton between the electric signals of the respective channels, said spatial filter means comprising adder means for inverting signs of the electric signals to alternate ones of the channels and for summing the inverted sign electric signals with remaining non-inverted sign electric signals.

2. The apparatus of claim 1 wherein the deriving means comprises:
(a) generating means for generating a pair of first and second complex conjugate reference signals having a frequency which equals a predetermiend integer times a repetition frequency of the emitted ultrasonic wave beam pulses;
(c) first mixing means for mixing the first reference signal and an output signal from said adder means and thereby converting the output signal from said adder means into a first complex received signal;
(c) second mixing means for mixing the second reference signal and the output signal from said adder means and thereby converting the output signal from said adder means into a second complex received signal;
(d) a first delay circuit delaying the first complex received signal and thereby deriving a first delayed complex received signal;
(e) a second delay circuit delaying the second complex received signal and thereby deriving a second delayed complex received signal; and
(f) an autocorrelator determining an autocorrelation function on the basis of the first and second non-delayed complex received signals and the first and second delayed complex received signals.

3. The apparatus of claim 2 further comprising weighting means for weighting the electric signals and outputting the weighted electric signal to said adder means.

4. The apparatus of claim 1 wherein the deriving means comprises:
(a) generating means for generating a pair of first and second complex conjugate reference signals having a frequency which equals a predetermined integer times a repetition frequency of the emitted ultrasonic wave beam pulses;
(b) first mixing means for mixing the first reference signal and an output signal from said adder means and thereby converting the output signal from said adder means into a first complex received signal;
(c) second mixing means for mixing the second reference signal and the output signal from said adder means and thereby converting the output signal from said adder means into a second complex received signal;
(d) a freqeuncy analyzer means for determining a frequency spectrum on the basis of the first and second complex received signals; and
(e) means for calculating an average value of the frequency spectrum.

5. The aparatus of claim 4 further comprising weighting means for weighting the electric signals and outputting the weighted electric signals to said adder means.

6. The apparatus of claim 1 wherein the deriving means comprises means for delaying the electric signals and thereby deriving delayed electric signals of the respective channels, and a spatiotemporal correlator determining a spatiotemporal correlation function on the basis of the electric signals of the respective channels and the delayed electric signals of the respective channels.

7. The apparatus of claim 1 wherein the deriving means comprises:
(a) means for weighting the electric signals and thereby deriving corresponding weighted electric signals;
(b) said adder means comprising a pair of adders inverting said signs of alternate ones of pairs of the electric signals of adjacent channels and summing the inverted electric signals and the remaining non-inverted electric signals, the adders thereby converting the electric signals into a pair of complex received signals having respective phases spatially different from each other by 90°;
(c) a frequency analyzer determining a frequency spectrum on the basis of the first and second complex received signals; and
(d) means for calculating an average value of the frequency spectrum.

8. An ultrasonic diagnostic apparatus comprising:
(a) means for emitting pulses of an ultrasonic wave beam into a body at a predetermined repetition period;
(b) means for receiving echo pulses of the ultrasonic wave beam via a plurality of different channels, and for simultaneously converting each of the received pulses into corresponding electric signals of the respective channels;
(c) first deriving means for deriving a time-dependent change in a variation between the electric signals of the respective channels;
(d) component calculating means for calculating a component of a speed of moving matter within the body in a first predetermined direction on the basis of the derived time-dependent change, wherein the moving matter causes the echo pulses and wherein the first predetermined direction is perpendicular to a direction of travel of the ultrasonic wave beam pulses;
(e) second deriving means for deriving a variation in phases of the electric signals;
(f) average calculating means for calculating an average value of the phase variation; and
(g) second component calculating means for calculating a component of the speed of the moving matter in a second predetermined direction on the basis of the calculated average value of the phase variation, wherein the second predetermined direction is parallel to the direction of the travel of the ultrasonic wave beam pulses,
wherein said first deriving means comprises spatial filter means for detecting a condition of the variation between the electric signals of the respective channels, said spatial filter means comprising adder means for inverting signs of the electric signals of alternate ones of the channels and for summing the inverted sign electric signals with remaining non-inverted sign electric signals.

9. The apparatus of claim 8 wherein the first deriving means comprises:
(a) generating means for generating a pair of first and second complex conjugate reference signals having a frequency which equals a predetermiend interger times a repetition frequency of the emitted ultrasonic wave beam pulses;
(b) first mixing means for mixing the first reference signal and an output signal from said adder means and thereby converting the output signal from said adder means into a first complex received signal;
(c) second mixing means for mixing the second reference signal and the output signal from said adder means and thereby converting the output signal from said adder means into a second complex received signal;
(d) a first delay circuit delaying the first complex received signal and thereby deriving a first delayed complex received signal;
(e) a second delay circuit delaying the second complex received signal and thereby deriving a second delayed complex received signal; and
(f) an autocorrelator determinnig an autocorrelation function on the basis of the first and second complex non-delayed received signals and the first and second delayed complex received signals.

10. The apparatus of claim 9 further comprising weighting means for weighting the electric signals and outputting the weighted electric signals to said adder means.

11. The apparatus of claim 8 wherein the second deriving means comprises:
(a) a phasing circuit adjusting phases of the electric signals and combining the phase-adjusted electric signals;
(b) generating means for generating a pair of first and second complex conjugate reference signals having a frequency which equals a predetermined integer times a repetition frequency of the emitted ultrasonic wave beam pulses;
(c) first mixing means for mixing the first reference signal and an output signal from the phasing circuit and thereby converting the output signal from the phasing circuit into a first complex received signal;
(d) second mixing means for mixing the second reference signal and the outout signal from the phasing circuit and thereby converting the output signal from the phasing circuit into a second complex received signal;
(e) a first delay circuit delaying the first complex received signal and thereby deriving a first delayed complex received signal;
(f) a second delay circuit delaying the second complex received signal and thereby deriving a second delayed complex received signal; and
(g) an autocorrelator determining an autocorrelation function on the basis of the first and second non-delayed complex received signals and the first and second delayed complex received signals.

12. The apparatus of claim 8 wherein the first deriving means comprises:
(a) generating means for generating a pair of first and second complex conjugate reference signals having a frequency which equals a predetermined integer times a repetition frequency of the emitted ultrasonic wave beam pulses;
(b) first mixing means for mixing the first reference signal and an output signal from said adder means and thereby converting the output signal from said adder means into a first complex received signal;
(c) second mixing means for mixing the second reference signal and the output signal from said adder means and thereby converting the output signal from said adder means into a second complex received signal;
(d) a frequency analyzer means for determining a frequency spectrum on the basis of the first and second complex received signals; and
(e) means for calculating an average value of the frequency spectrum.

13. The apparatus of claim 12 further comprising weighting means for weighting the electric signals and outputting the weighted electric signals to said adder means.

14. The apparatus of claim 8 wherein the second deriving means comprises:
(a) a phasing circuit adjusting phases of the electric signals and combining the phase-adjusted electric signals;
(b) generating means for generating a pair of first and second complex conjugate reference signals having a frequency which equals a predetermined integer times a repetition frequency of the emitted ultrasonic wave beam pulses;
(c) first mixing means for mixing the first reference signal and an output signal from the phasing circuit and thereby converting the output signal from the phasing circuit into a first complex received signal;
(d) second mixing means for mixing the second reference signal and the output signal from the phasing circuit and thereby converting the output signal from the phasing circuit into a second complex received signal;
(e) a frequency analyzer means for determining a frequency spectrum on the basis of the first and second complex received signals; and
(f) means for calculating an average value of the frequency spectrum.

15. The apparatus of claim 8 wherein the first deriving means comprises means for delaying the electric signals and thereby deriving delayed electric signals of the respective channels, and a spatiotemporal correlator determining a spatiotemporal correlation function on the basis of the non-delayed electric signals of the respective channels and the delayed electric signals of the respective channels.

16. The apparatus of claim 8 wherein the first deriving means comprises:
(a) means for weighting the electric signals and thereby deriving corresponding weighted electric signals;
(b) said adder means comprising a pair of adders inverting said signs of alternate ones of pairs of the electric signals of adjacent channels and summing the inverted electric signals and the remaining non-inverted electric signals, the adders thereby converting the electric signals into a pair of complex received signals having respective phases spatially different from each other by 90°;
(c) a frequency analyzer determining a frequency spectrum on the basis of the first and second complex received signals; and
(d) means for calculating an average value of the frequency spectrum.

17. An ultrasonic diagnostic apparatus comprising:
(a) means for emitting pulses of an ultrasonic wave beam into a body at a predetermined repetition period;
(b) means for receiving echo pulses of the ultrasonic wave beam via a plurality of different channels, and for simultaneously converting each of the received pulses into corresponding electric signals of the respective channels;

(c) first deriving means for deriving a time-dependent change in a variation between the electric signals of the respective channels; and (d) calculating means for calculating a component of a speed of moving matter within the body in a predetermined direction on the basis of the derived time-dependent change, wherein the moving matter causes the echo pulses and wherein the predetermined direction is perpendicular to a direction of travel of the ultrasonic wave beam pulses;

wherein said deriving means comprises spatial filter means for detecting a condition of the variation between the electric signals of the respective channels, said spatial filter means comprising a plurality of adders for inverting signs of alternate ones of pairs of the electric signals of adjacent channels and for summing the inverted sign electric signals with remaining non-inverted sign electric signals.

18. An ultrasonic diagnostic apparatus cmoprising:

(a) means for emitting pulses of an ultrasonic wave beam into a body at a predetermined repetition period;

(b) means for receiving echo pulses of the ultrasonic wave beam via a plurality of different channels, and for simultaneously converting each of the received pulses into corresponding electric signals of the respective channels;

(c) first deriving means for deriving a time-dependent change in a variation between the electric signals of the respective channels;

(d) first component calculating means for calculating a component of a speed of moving matter within the body in a first predetermined direction on the basis of the deived time-dependent change, wherein the moving matter causes the echo pulses and wherein the first predetermined direction is perpendicular to a direction of travel of the ultrasonic wave beam pulses;

(e) second deriving means for deriving a variation in phases of the electric signals;

(f) average calculating means for calculating an average value of the phase variation; and (g) second component calculating means for calculating a component of the speed of the moving matter in a second predetermined direction on the basis of the calculated average value of the phase variation, wherein the second predetermined direction is parallel to the direction of the travel of the ultrasonic wave beam pulses, wherein said first deriving means comprises spatial filter means for detecting a condition of the variation between the electric signals of the respective channels, said spatial filter means comprising a plurality of adders for inverting signs of alternate ones of pairs of the electric signals of adjacent channels and for summing the inverted sign electric signals with remaining non-inverted sign electric signals.

* * * * *